(12) United States Patent
Fernkvist et al.

(10) Patent No.: US 6,398,769 B1
(45) Date of Patent: Jun. 4, 2002

(54) ABSORPTION MATERIAL HAVING TEMPERATURE DEPENDENT ABSORPTION CAPACITY AND THE USE THEREOF IN AN ABSORBENT ARTICLE

(75) Inventors: Maria Fernkvist, Mölndal; Thami Chihani, Mölnlycke, both of (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/284,632

(22) PCT Filed: Oct. 17, 1999

(86) PCT No.: PCT/SE97/01740

§ 371 (c)(1),
(2), (4) Date: Apr. 15, 1999

(87) PCT Pub. No.: WO98/18505

PCT Pub. Date: May 7, 1998

(30) Foreign Application Priority Data

Oct. 28, 1996 (SE) ................................. 9603919

(51) Int. Cl.[7] .......................... A61F 13/15; A61F 13/20
(52) U.S. Cl. ................. 604/385.01; 604/358; 604/366; 604/370; 604/378; 604/381; 525/329.9; 525/330.1
(58) Field of Search .................. 604/358, 364, 604/365, 366, 367, 374, 385.01; 525/329.9, 330.1, 330.3

(56) References Cited

U.S. PATENT DOCUMENTS

| | | | | |
|---|---|---|---|---|
| 5,015,245 A | * | 5/1991 | Noda | 604/367 |
| 5,102,597 A | * | 4/1992 | Roe et al. | 264/126 |
| 5,124,188 A | * | 6/1992 | Roe et al. | 428/72 |
| 5,180,622 A | * | 1/1993 | Berg et al. | 428/192 |
| 5,190,533 A | * | 3/1993 | Blackburn | 604/367 |
| 5,393,602 A | * | 2/1995 | Urry | 428/290 |
| 5,800,418 A | * | 9/1998 | Ahr | 604/368 |

FOREIGN PATENT DOCUMENTS

EP  0 693 508  1/1996

* cited by examiner

Primary Examiner—John G. Weiss
Assistant Examiner—Michele Kidwell
(74) Attorney, Agent, or Firm—Burns, Doane, Swecker & Mathis, L.L.P.

(57) ABSTRACT

The invention relates to an absorption material (50; 60) comprising a carrier material exhibiting a coating (51; 61) of a thermosensitive polymer with a cloud point at a temperature in the vicinity of and somewhat below the body temperature of a healthy human being. The absorption properties of the polymer change at the cloud point, so that the polymer substantially lacks absorption capacity at a first temperature on one side of the cloud point but exhibits good absorption properties at a second temperature on the other side of the cloud point. Furthermore, the invention includes an absorbent article such as a diaper, an incontinence protector, a sanitary napkin, or the like, having an absorption body comprising an absorption material coated with a thermosensitive polymer.

27 Claims, 4 Drawing Sheets

ABSORPTION MATERIAL HAVING TEMPERATURE DEPENDENT ABSORPTION CAPACITY AND THE USE THEREOF IN AN ABSORBENT ARTICLE

TECHNICAL FIELD

The invention pertains to an absorption material for use in an absorbent article such as a diaper, an incontinence protector, a sanitary napkin or the like. The invention further relates to an absorbent article comprising the absorption material.

BACKGROUND OF THE INVENTION

Absorbent articles such as diapers, incontinence protectors, sanitary napkins, bed protectors, seat covers, or the like generally comprise an absorption body which is constituted by one or several layers of absorption material. Usually, the absorption material mainly consists of cellulose fluff pulp. When such an absorption body is wetted, the area of the absorption body which is first hit by liquid will absorb substantially all the liquid. Thereby, this area will be saturated with liquid and when subsequent wettings occur the absorption body will not have sufficient capacity in order to absorb all the emitted body liquid. As a result, liquid will flow out over the surface of the article and leak out past the edges of the article.

In order to overcome such leakage, it has been suggested to provide the absorption body with compression patterns of different kinds, thereby increasing the liquid distributing ability of the article. An example of such a compression pattern is grooves which extend in the longitudinal direction of the article. Since the finer capillaries in the compressed portions of the absorption body transport liquid better than surrounding portions of the absorption body, it is possible to obtain, in this manner, a certain degree of draining of the initially wetted area of the absorption body. However, the transportation of liquid is dependent on capillary action, which is a slow process, meaning that the draining of the wetted area will often be incomplete and insufficient.

Another way to reduce the risk of leakage, occurring as a result of the initially wetted area of an absorption body being saturated with liquid, is to increase the amount of absorption material in the acquisition area. Although it is possible to increase the leakage security of the article in this manner, such a solution still presents some drawbacks. When the absorption material consists of cellulose fluff pulp, an increased amount of absorption material will make the article thick and bulky in the acquisition area. Since the acquisition area of body-worn absorbent articles should be accommodated in the crotch portion of the wearer, between the legs of the wearer, such a thick and bulky article may be perceived as being uncomfortable to wear. In addition, it is difficult to conceal a voluminous article under ordinary clothing, which means that adult wearers, in particular, are reluctant to wear such articles since they are perceived As embarrassing.

An alternative way to increase the absorption capacity in the acquisition area is to use what is known as superabsorbent material, i.e. polymers having the ability to absorb liquid in an amount corresponding to several times their own weight. Such superabsorbents absorb liquid by chemically binding it in a gel. When absorption has taken place, the liquid remains in the gel and will not be transported any further. This implies that superabsorbent materials incorporated into an absorbent structure greatly reduce the liquid spreading in the structure and contribute to a poor utilization of absorption material which is positioned at a distance from the area which is initially hit by emitted body fluid.

Furthermore, concentrating the absorption material to the initially wetted area of an absorbent article means that liquid will remain in close contact with the body of the user. For this reason, such an article may be perceived as being wet and uncomfortable to wear after wetting, even if the absorption capacity of the article has not yet been fully used. Another drawback, in connection with liquid which remains in the vicinity of the body of the wearer, is that moisture from the article may cause irritation of the wearer's skin.

PURPOSE OF THE INVENTION

One purpose of the present invention has been to offer a possibility of directing and controlling the absorption and the liquid distribution in an absorbent article of the kind mentioned in the introduction. A further purpose of the invention is to achieve an absorbent article having high leakage security and which makes better use of the available absorption capacity. An objective of the invention has also been to offer an absorption material which makes it possible to obtain controlled absorption and liquid distribution in an absorbent article.

SUMMARY OF THE INVENTION

An absorption material in accordance with the invention is primarily characterized in that the material comprises a carrier material exhibiting a coating of a thermosensitive polymer, which polymer exhibits a cloud point at a temperature in the vicinity of and somewhat below the body temperature of a healthy human being, wherein the surface structure and the chemical properties of the surface of the polymer change at the cloud point, whereby the absorption material substantially lacks absorption capacity at a first temperature on one side of the cloud point but exhibits good absorption capacity at a second temperature on the other side of the cloud point.

The thermosensitive coating on the absorption material in accordance with the invention implies that the temperature of the surroundings of the absorption material determines whether the absorption material is available for absorption. The thickness of the coating may be used in order to control the absorption characteristics of the absorption material and can, accordingly, be anything from a mono-layer of thermosensitive polymer to a thick coating.

When the absorption material is used in an absorbent article intended for absorption of body fluids, the temperature of the fluid which reaches the absorbent article will determine whether or not the fluid will be absorbed. Thereby, the thermosensitive material may either be of a kind which is non-absorbent at a temperature higher than the cloud point, but absorbent at a temperature below the cloud point, or vice versa. In both cases the cloud point should be somewhat below the body temperature of a healthy human being, in the first instance preferably 2–7° C. below and most preferably 2–3° C. below. In the second instance the cloud point may be a few centigrades further below, whereby absorption will continue during a longer period of time while the body fluids are cooling down.

Accordingly, the cloud point should be between 28° C. and 35° C., and preferably between 32° C. and 34° C.

Thermosensitive polymers having suitable properties are, for instance, derivatives of cellulose such as ethylhydroxyethyl cellulose (EHEC). Other suitable polymers are acrylamides such as poly-n-isopropyl acrylamide (PNIPAM), poly-n-n-methacrylamide, poly-n-n-propyl methacrylamide and poly-n-n-diethyl acrylamide. Another large family of polymers having cloud points lying within the temperature ranges which are suitable for the present purpose are polyethylene glycols and co-polymers thereof. Furthermore, branched polymers containing ethyleneoxide blocks may be used.

The carrier material comprised in the absorption material may consist wholly or partly of fluffed cellulosic fibres or of superabsorbent material in the form of particles such as flakes, fibres, grains, granules or the like.

In addition, the coated absorption material may consist of a combination of superabsorbent material and fluffed cellulose fibres, or other absorbent fibres such as cotton, viscose, or the like. It is further possible, in accordance with the invention, to coat non-absorbent, hydrophobic fibres with a thermosensitive polymer. An absorbent material of this kind will preferably have no absorption capacity when it is first wetted by body fluid, but will be able to absorb small quantities of residual fluid when the temperature of the fluid decreases below the cloud point of the polymer. Material of this kind may be used as liquid-permeable acquisition and distance layers between a covering layer and an absorption body of an absorbent article, or may be a component in the liquid-permeable covering layer of the article. Even if the fibrous structure is comparatively hydrophobic, small amounts of liquid may be retained between the fibres after wetting. An advantage of using a material in accordance with the invention close to the surface of an absorbent article is that the surface dryness of the article between wettings may be considerably improved.

The absorption material may be provided in the form of a bonded or unbonded fibre mat, in the form of a multilayered structure with mutually different material composition and/or different absorption properties.

In accordance with the invention, an absorbent article such as a diaper, an incontinence protector, a sanitary napkin or the like, exhibiting an absorption body enclosed in a partially liquid-pervious cover, is primarily characterized in that the absorption body comprises absorption material which comprises a carrier material exhibiting a coating of a thermosensitive polymer, which polymer exhibits a cloud point at a temperature in the vicinity of and slightly below the body temperature of a healthy human being, wherein the absorption properties of the polymer change at the cloud point so that the polymer substantially lacks absorption capacity at a first temperature on one side of the cloud point, but exhibits good absorption capacity at a second temperature on the other side of the cloud point.

In accordance with the invention, the absorption body of the absorbent article may be constituted in a number of different ways. A cover for an absorbent article of the intended kind is generally constituted by a liquid-permeable layer and a liquid-impervious layer which are mutually connected around the absorption body of the article and together enclose the absorption body. According to one embodiment of the invention, the absorption body in such an article may thereby comprise a first absorption layer arranged closest to the liquid-permeable layer and mainly consisting of the absorption material coated with the thermosensitive polymer, and a second absorption layer arranged closest to the liquid-impervious layer and mainly consisting of absorbent material without thermosensitive coating.

According to another embodiment, the absorption body comprises an absorption layer exhibiting longitudinal bands, wherein bands mainly consisting of the absorption material coated with the thermosensitive polymer alternate with bands mainly consisting of absorbent material without thermosensitive coating.

The absorption material coated with the thermosensitive polymer is preferably primarily arranged at the crotch portion of the article.

BRIEF DESCRIPTION OF THE DRAWINGS

In the following, the invention will be described in greater detail with reference to the figures which are shown in the attached drawings.

DETAILED DESCRIPTION OF PREFERRED EMBODIMENTS

Figure 1:
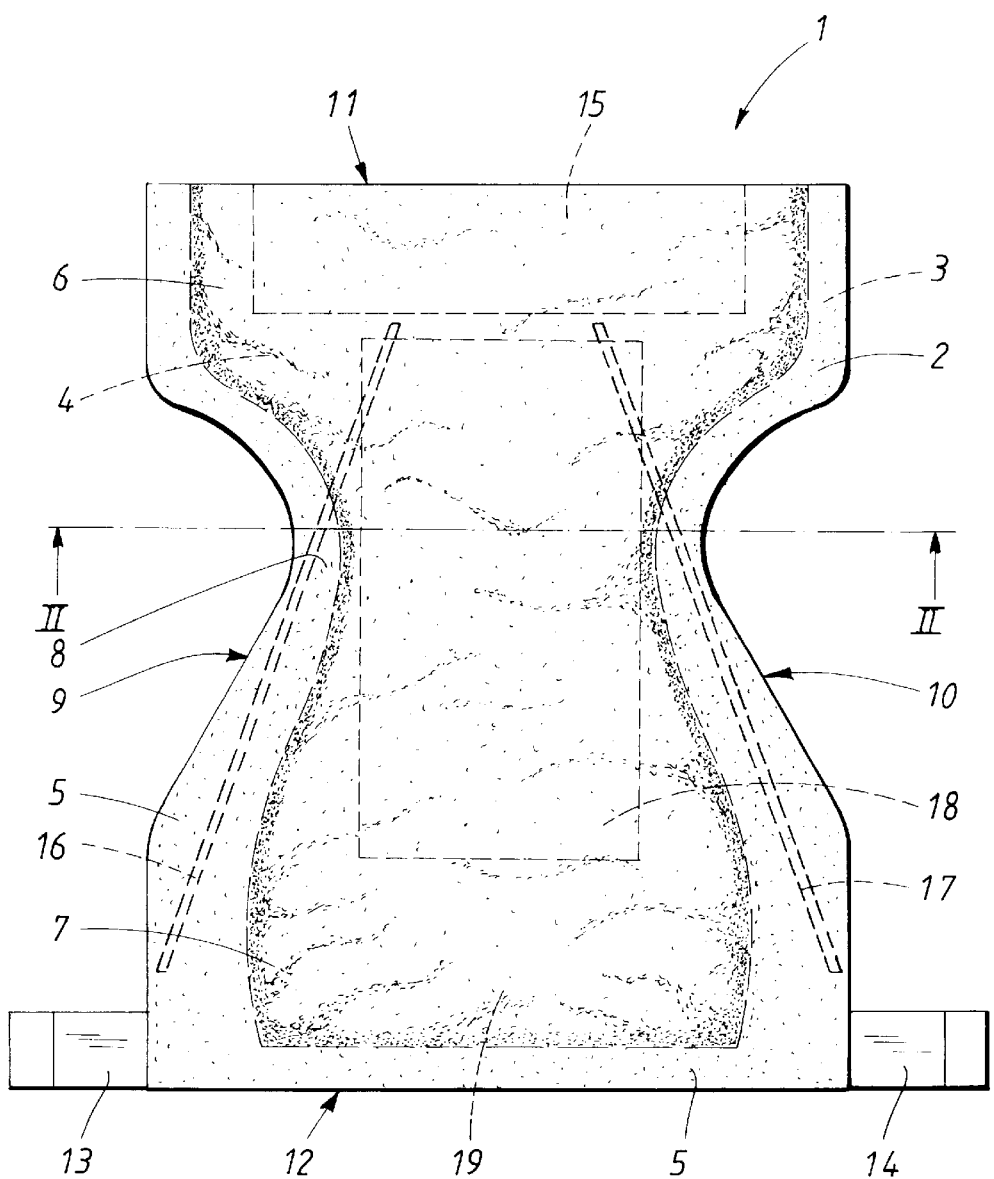
FIG. 1 shows a diaper according to a first embodiment of the invention.
Figure 2:
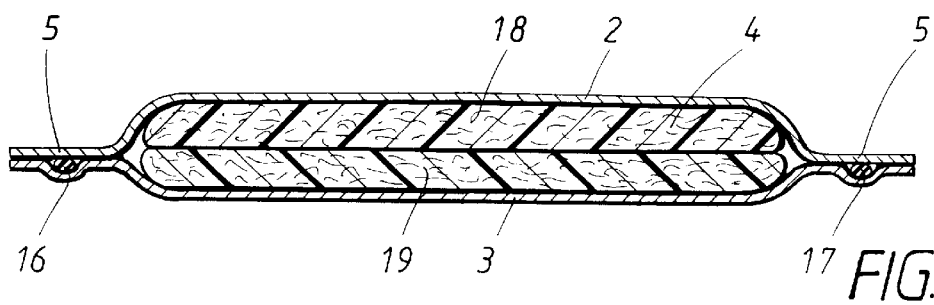
FIG. 2 shows a section along the line II—II through the diaper in FIG. 1.

The diaper 1 shown in FIGS. 1 and 2 comprises a liquid-permeable covering layer 2, which is intended to be facing the user during use, a liquid-impervious covering layer 3, which is intended to be facing away from the user during use, and an absorption body 4, enclosed between the two covering layers, intended to receive and absorb the body fluid which is emitted to the diaper during use. The covering layers 2, 3 extend out around the absorption body 4 and are mutually connected within the protruding portions 5 by, for example, gluing or welding by means of heat or ultrasonics.

The diaper 1 has a substantially elongate shape, with wider front and rear portions 6, 7, and a narrower intermediate crotch portion 8. Thereby, the front portion 6 is the part of the diaper 1 which is intended to be facing forwards on the user when the diaper is used and the rear portion 7 is the part of the diaper which is turned backwards on the user. Furthermore, the diaper 1 has two longitudinal, concavely-curved side edges 9, 10 and a front edge 11 and a rear edge 12.

The diaper 1 is of the sort which is attached together during use so that it encloses the lower portion of the torso of the user in a pant-like way. For this purpose a tape flap 13, 14 is arranged protruding from each side edge 9, 10, alongside the rear edge 12 of the diaper. The tape flaps 13, 14 are intended to interact with a receiving area 15 arranged on the liquid-impervious covering layer 3 on the front portion 6 of the diaper 1. Such a receiving area 15 suitably exhibits some kind of reinforcement, for example in the form of an additional plastic layer, or a coating applied on the liquid-impervious covering layer 3. It is of course also conceivable to use other types of attachment devices for the diaper 1, such as buttons and buttonholes, hooks and eyes, snap fasteners, hook-and-loop fasteners or the like.

The diaper 1 is further provided with pre-tensionally applied, longitudinal elastic members 16, 17, arranged in a generally V-shaped pattern, with the tip of the V directed towards the front edge 11 of the diaper and the two legs directed towards the rear edge 12 of the diaper. The elastic members 16, 17 shape the diaper 1 according to the body of the user and constitute its leg elastics during use. In this way, the elastic members 16, 17 serve to keep the side edges 9, 10 of the diaper in contact with the legs of the user in order to prevent gaps arising between the diaper and the body of the user during use, through which body fluid may leak out from the diaper.

The absorption body 4 of the diaper 1 exhibits a first absorption layer 18 arranged immediately inside the liquid-permeable covering layer 2, and a second absorption layer 19 arranged immediately inside the liquid-impervious covering layer 3. The first absorption layer 18 has a rectangular shape and is slightly smaller than the second absorption layer 19 which has substantially the same shape as the diaper 1. The first absorption layer 18 is placed within the area of the diaper which is expected to be hit first by body fluid when the diaper is used. Obviously, the shape of the absorption layers is of no decisive importance for the invention, a number of further shapes and dimension conditions also being conceivable.

The first absorption layer 18 is primarily or completely constituted by an absorption material in accordance with the invention. Accordingly, the first absorption layer may consist of cellulose fluff pulp, or other hydrophillic fibres which are treated so that they exhibit a coating of a thermosensitive polymer.

Alternatively, the first absorption layer 18 consists of a mixture of an absorbent or non-absorbent fibre material which comprises superabsorbent material with a coating of thermosensitive polymer. Examples of such fibre materials which can serve as carrier materials for the superabsorbent material are conventional layers of cellulose fluff pulp, different types of bonded fibre fabrics, so-called nonwoven materials, bonded or unbonded waddings, or the like. Furthermore, the carrier material may of course be constituted by a fibre mat of hydrophillic fibres exhibiting a coating of thermosensitive polymer.

Examples of thermosensitive polymers which may be used for coating superabsorbent materials and other types of absorbent materials are cellulose derivatives such as ethylhydroxyethyl cellulose (EHEC), poly-n-isopropyl acrylamide (PNIPAM) and polyethylene glycols. In order to have the intended effect, the thermosensitive polymer must have a cloud point at a temperature in the vicinity of and preferably somewhat below the body temperature of a healthy human being. Accordingly, the cloud point $C_p$ should be between 28° C. and 35° C., preferably between 32° C. and 34° C. At a temperature above the cloud point the listed polymers lack absorption capacity, while at a temperature below the cloud point they have a good absorption capacity. This implies that absorption materials exhibiting a coating of a thermosensitive polymer of this type are not available for absorption of recently emitted body fluid when the temperature of the body fluid is above the cloud point. As soon as the temperature of the body fluid decreases below the cloud point of the thermosensitive polymer, the polymer starts to absorb. At the same time, the absorption material inside the coating becomes available for absorption of body fluid. Such absorption proceeds until a renewed wetting takes place, so that the temperature once again rises above the cloud point of the thermosensitive polymer and the transport of liquid into the absorption material inside the thermosensitive polymer ceases.

The liquid which has been absorbed into the absorption material coated with thermosensitive polymer remains inside the absorption material and cannot penetrate back out past the thermosensitive polymer when this is not in its absorbent state. In contrast to this, the absorption capacity of the thermosensitive polymer is reversible, which implies that when the temperature decreases, the polymer starts to absorb and swells slightly during the absorption. When the temperature during a renewed wetting is raised above the cloud point, the polymer shrinks and emits the liquid which has been absorbed at the lower temperature.

The first absorption layer 18 preferably has a lower density than the second absorption layer 19 and is intended to rapidly let body fluid pass through to the second absorption layer 19.

The second absorption layer 19 may consist of any conventional absorption material suitable for the purpose such as cellulose fluff pulp, absorbent nonwoven, tissue layers, or the like.

By means of their mutually different properties, the two absorption layers 18, 19 fulfill different functions. Thus, the first absorption layer serves as an acquisition layer for the liquid which is emitted to the diaper 1. The first absorption layer 18 should be able to rapidly receive large liquid quantities during a short period of time, i.e. have a high instantaneous liquid absorption capacity. The layer 18 should further be able to retain the liquid until it is successively absorbed by the second absorption layer 19. The second absorption layer 19 constitutes a storage and distribution layer for the liquid. The liquid which is absorbed by the second absorption layer 19 is distributed through the capillary structure of the layer, away from the region of the layer which is first wetted by the liquid. In this way, new liquid may gradually be absorbed from the first absorption layer 18.

When body fluid is emitted to the diaper 1, the liquid first passes through the liquid-permeable covering layer 2, in to the first absorption layer 18. When the body fluid leaves the user it has a temperature in the vicinity of the body temperature, i.e. between 35° C. and 37° C. At such a temperature, the thermosensitive polymer is non-absorbent, whereby the main part of the body fluid may pass through the first absorption layer 18 and be absorbed by the second absorption layer 19.

As the body fluid cools down, the cloud point of the thermosensitive polymer is passed and body fluid, which has not been drained from the first absorption layer 18 to the second absorption layer 19, may be absorbed by the absorption material coated with thermosensitive polymer in the first absorption layer 18. In this way, the first absorption layer 18 is effectively emptied from remaining liquid and the network structure in the layer 18 becomes available for receiving a new quantity of liquid. At the same time, the risk that remaining liquid in the first absorbent layer 18 should be pressed back in a direction towards the body of the user is reduced. In this way, the skin of the user may thus be kept substantially dry even after wetting of the diaper 1, as a result of which the risk of skin irritation or other discomfort caused by a wet surface on the diaper has been more or less eliminated.

Figure 3:
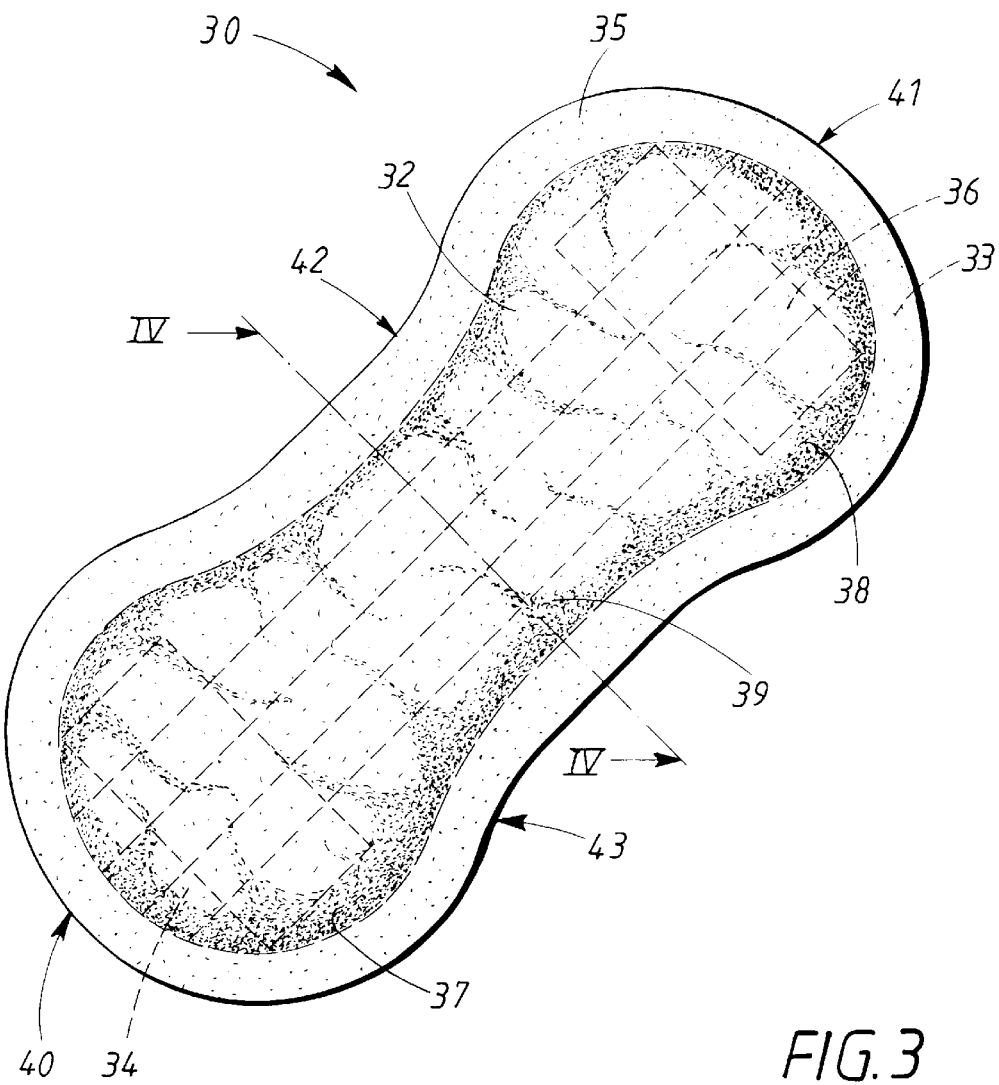
FIG. 3 shows an incontinence protector according to a second embodiment of the invention.
Figure 4:
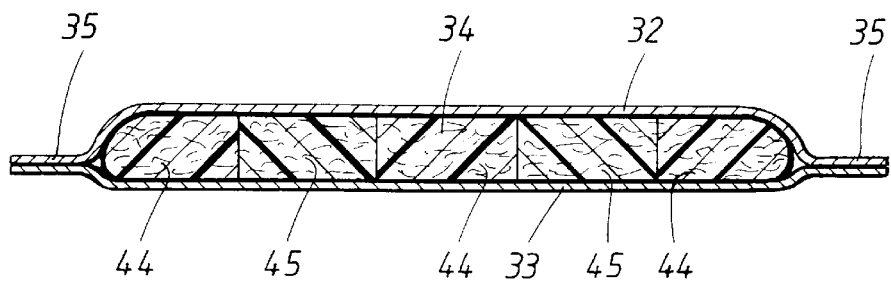
FIG. 4 shows a section along the line IV—IV through the incontinence protector in FIG. 3.

The incontinence protector 30 shown in FIGS. 3 and 4 comprises a liquid-permeable covering layer 32, a liquid-impervious covering layer 33, and an absorbent body 34 enclosed between the covering layers 32, 33. The liquid-permeable covering layer 32 is constituted, for example, by a layer of non-woven fibre fabric, so-called nonwoven material, or a perforated plastic film, scrim material, or the like. The liquid-impervious covering layer 33 may consist of a liquid-impervious plastic film, a nonwoven layer which has been coated with a liquid barrier material, or any other easily pliable material layer which has the ability to resist liquid penetration. As a rule, it is an advantage if the liquid-impervious covering layer 33 exhibits a certain breathability, i.e. allows passage of water vapour through the layer 33. The two covering layers 32, 33 have a slightly larger extension in the plane than the absorbent body 34 and extend a distance out past the absorption body 34 around the entire periphery of this. The covering layers 32, 33 are mutually connected within the projecting portions 35, for example by gluing or welding by means of heat or ultrasonics.

On the outside of the liquid-impervious covering layer 33, an attachment member 36 is arranged in the form of two transverse regions of self-adhesive glue. Before use, the attachment member 36 is suitably covered by a detachable covering layer, not shown in the drawing, made of paper treated with release agent, plastic film, or the like. Instead of the shown adhesive pattern in the form of two transverse glue regions, a number of other adhesive patterns may be used, such as one or several longitudinal regions, dots, complete coverage etc. Alternatively, other types of attachment members may be utilized, such as hook-and-loop fastener surfaces, snap fasteners, girdles, special pants, or the like.

An incontinence protector 30 of the sort shown in FIGS. 3 and 4 is primarily intended to be used by persons with comparatively light incontinence troubles and therefore has such a size that it can be easily accommodated inside a pair of conventional pants. Thereby, the attachment member 36 serves to keep the incontinence protector in place inside the pants during use.

The incontinence protector 30 is substantially hourglass-shaped, with wider end portions 37, 38 and a narrower crotch portion 39 located between the end portions 37, 38. The crotch portion 39 is the portion of the incontinence protector 30 which is intended to be applied in the crotch of the user during use and to serve as a receiving surface for the body fluid which is emitted to the incontinence protector 30. Furthermore, the incontinence protector 30 exhibits two transverse rounded end edges 40, 41, and two longitudinal curved side edges 42, 43 extending between the end edges 40, 41.

The absorption body 34 is divided into longitudinal bands, whereby alternating bands 44, 45 are, respectively, mainly constituted by conventional absorption material, and mainly constituted by absorption material with a coating of thermosensitive polymer, of the sort which has been described in connection with the diaper 1 in FIGS. 1 and 2.

Thereby, the bands 45 which mainly consist of conventional absorption material suitably exhibit better liquid distributing ability than the bands 44 which mainly consist of absorption material with a thermosensitive coating. The liquid transport primarily takes place in the first-mentioned bands 45, while the latter bands 44 serve as liquid reservoirs for body fluid which has not yet been distributed in the absorbent structure.

Figure 5:
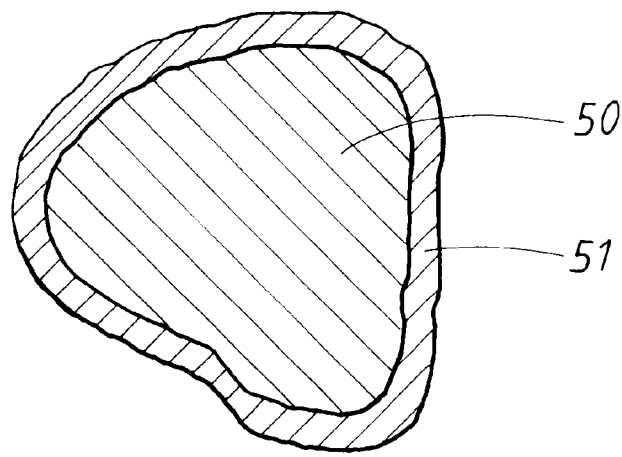
FIG. 5 and FIG. 6 show in cross-section an absorption material coated with thermosensitive polymer.
Figure 6:
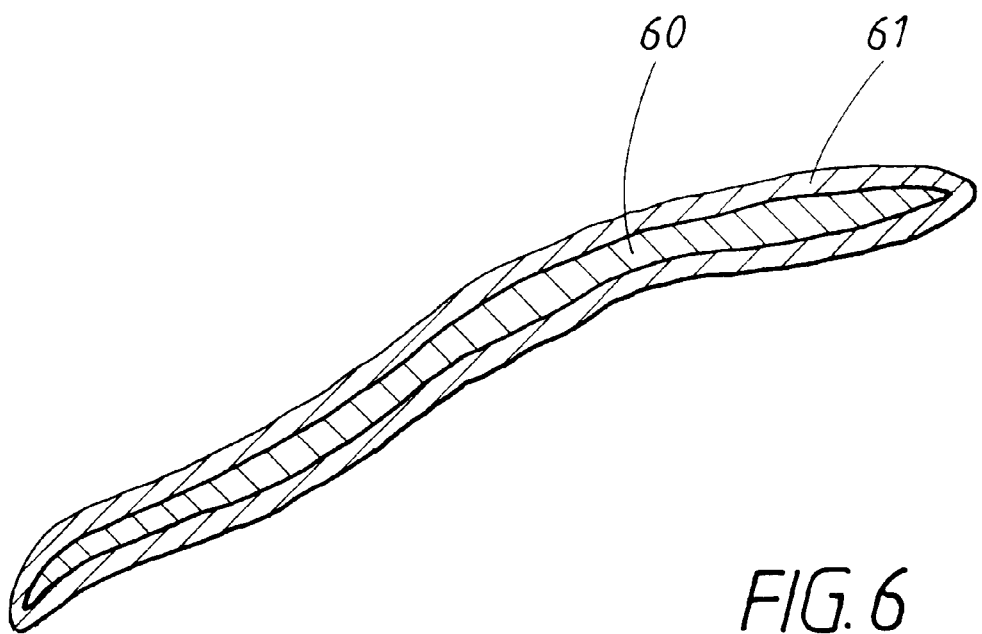

In FIGS. 5 and 6 is shown in cross-section a grain 50 of superabsorbent material and a cellulose fibre 60, respectively, which have been coated with a thin layer 51, 61 of thermosensitive polymer. The coating on the absorption material constitutes a barrier against absorption within a temperature range above the cloud point of the thermosensitive polymer. Accordingly, by means of the coating, it is possible to achieve a delayed absorption, controlled by the temperature of the liquid which reaches the absorption material.

The coating of the absorption material with thermosensitive polymer may be achieved by a number of well-known techniques, such as spraying or by treating the absorption material in a liquid suspension.

Figure 7:
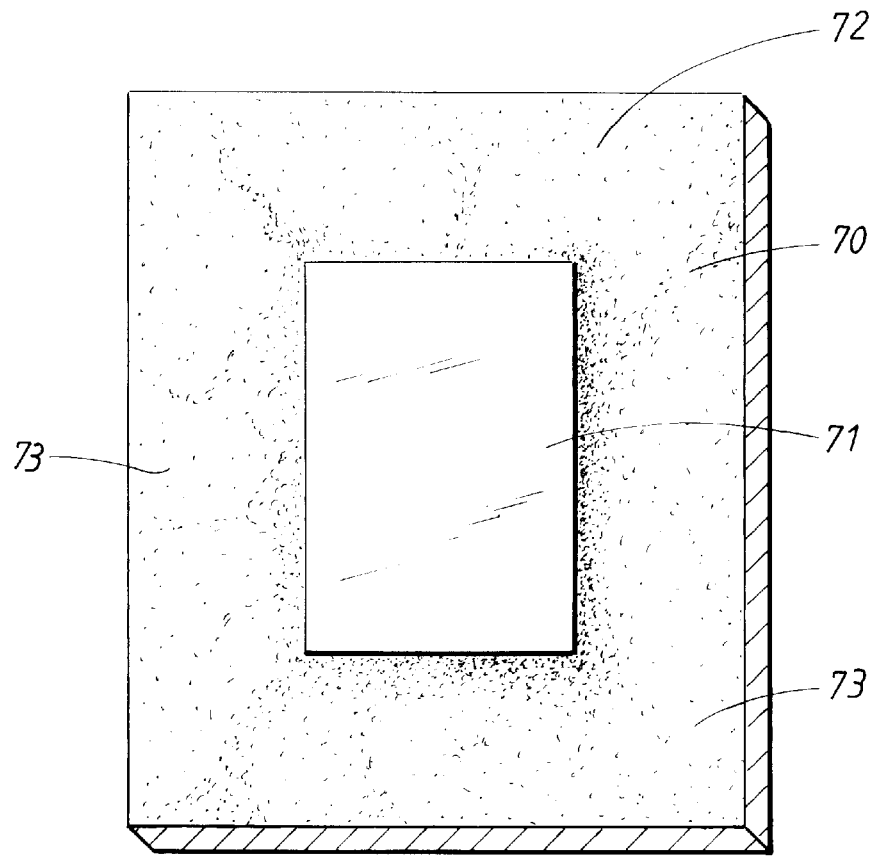
FIG. 7 shows an absorption body with a coating of thermosensitive polymer.
Figure 8:
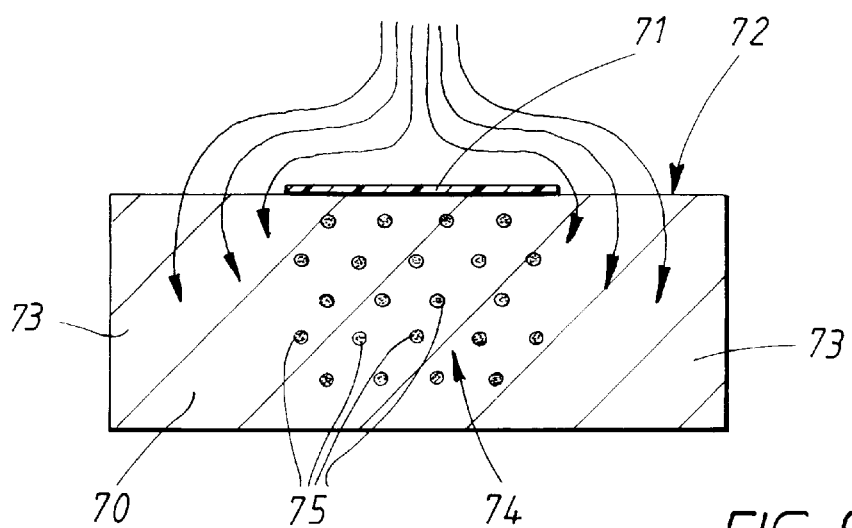
FIG. 8 shows a section along the line VIII–VIII through the absorption body in FIG. 7.

The absorption body 70 shown in FIGS. 7 and 8 is intended to be applied inside a conventional cover of an absorbent article, for example a diaper, a sanitary napkin, or an incontinence protector. The absorption body 70 exhibits a barrier region 71 which corresponds to the portion of the absorption body which during use is intended to be first wetted by liquid. Within the barrier region 71 a coating or a thin film of a thermosensitive polymer in accordance with the invention is applied on the surface 72 of the absorption body 70 which is facing the user during use. When the absorption body 70 is hit by body fluid (the liquid flow is indicated with arrows in FIG. 8), the liquid is prevented from penetrating into the absorption body in the barrier region 71 and instead forced to more peripheral parts of the absorption body 70. When the temperature of the body fluid decreases below the cloud point of the thermosensitive polymer it will, however, be possible for remaining liquid on the surface 72 of the absorption body 70 to be absorbed in through the barrier region 71.

By means of the barrier region 71, an improved liquid distribution in the absorption body is obtained and thereby a higher degree of utilization of the absorption material. A region 74 of the absorption body 70 inside the barrier region may advantageously contain superabsorbent material 75, which, by means of the barrier region 71 on the surf ace of the absorption body 72, is not available for instant absorption of body fluid. In this way, body fluid is prevented from being initially bonded by the superabsorbent 75 before liquid distribution to the remaining parts 73 of the absorbent structure has taken place. Accordingly, the superabsorbent material becomes available for absorption only when the temperature of the body fluid has decreased below the cloud point of the thermosensitive polymer. Some liquid is also brought by the capillary forces in the absorbent structure from the peripheral parts back into the region 74 inside the barrier region 71.

According to one embodiment of the invention, the barrier coating is at least partially soluble in the solution, whereby the coating gradually disappears after a first wetting. By means of such an embodiment, a relatively unused part of the absorption body is liberated for liquid acquisition before a second, or third wetting.

The invention should not be regarded as being limited to the herein described embodiments, but a number of further variants and modifications are possible within the scope of the following claims. Furthermore, all conceivable combinations of the described embodiments are intended to be embraced by the claims.

What is claimed is:

1. Absorbent article, comprising an absorption body enclosed in a partially liquid-permeable cover, wherein the absorption body comprises absorption material comprising a carrier material coated with a thermosensitive polymer, which polymer exhibits a cloud point at a temperature about and somewhat below the body temperature of a healthy human being, whereby absorption properties of the polymer change at the cloud point so that the polymer substantially lacks absorption capacity at a first temperature on one side of the cloud point but exhibits absorption capacity at a second temperature on the other side of the cloud point, wherein the cover comprises a liquid-permeable layer and a liquid-impervious layer which are mutually connected around the absorption body, wherein the absorption body comprises a first absorption layer and a second absorption layer, the first absorption layer is arranged between the liquid-permeable layer and the second absorption layer, the first absorption layer consists essentially of a carrier material coated with a thermosensitive polymer, the second absorption layer is arranged closest to the liquid-impervious layer, and the second absorption layer consists essentially of absorbent material without thermosensitive coating.

2. Absorption material according to claim 1, wherein the cloud point is between 28° C. and 35° C.

3. Absorption material according to claim 1, wherein the cloud point is between 32° C. and 34° C.

4. Absorption material according to claim 1, wherein the polymer lacks absorption capacity at a temperature higher than the cloud point, but exhibits absorption capacity at a temperature lower than the cloud point.

5. Absorption material according to claim 1, wherein the thermosensitive polymer is a cellulose derivative.

6. Absorption material according to claim 5, wherein the thermosensitive polymer is ethylhydroxyethyl cellulose.

7. Absorption material according to claim 1, wherein the thermosensitive polymer is an acrylamide.

8. Absorption material according to claim 7, wherein the thermosensitive polymer is one of poly-n-isopropyl acrylamide (PNIPAM), poly-n-propyl methacrylamide, and poly-n-diethyl acrylamyde.

9. Absorption material according to claim 1, wherein the thermosensitive polymer is an polyethylene glycol.

10. Absorption material according to claim 1, wherein the absorption material is provided in the form of a bonded, or unbonded fibre mat.

11. Absorption material according to claim 1, wherein the carrier material comprises superabsorbent material in the form of particles.

12. Absorption material according to claim 11, wherein the particles are flakes, fibres, grains, or granules.

13. Absorption material according to claim 1, wherein the carrier material comprises fluffed cellulosic fibres.

14. Absorption material according to claim 1, wherein the carrier material comprises non-absorbent hydrophobic fibres.

15. Absorbent article according to claim 1, and further exhibiting two end portions and a crotch portion located between the end portions, wherein the carrier material coated with the thermosensitive polymer primarily is arranged at the crotch portion of the article.

16. Absorption material according to claim 1, for use in a diaper.

17. Absorption material according to claim 1, for use in an incontinence protector.

18. Absorption material according to claim 1, for use in a sanitary napkin.

19. Absorbent article according to claim 11, wherein the absorbent article is a diaper.

20. Absorbent article according to claim 11, wherein the absorbent article is an incontinence protector.

21. Absorbent article according to claim 11, wherein the absorbent article is a sanitary napkin.

22. Absorption material according to claim 1, wherein the thermosensitive polymer is a branched polymer comprising ethyleneoxide-blocks.

23. Absorption body for use in an absorbent article wherein the absorption body comprises a liquid receiving surface, which in the absorbent article is intended to be facing a user, wherein a region of the liquid receiving surface includes a film or a coating of a thermosensitive polymer which exhibits a cloud point between 28° C. and 35° C., wherein the polymer lacks absorption capacity at a temperature higher than the cloud point, but exhibits absorption capacity at a temperature higher than the cloud point, wherein the absorption body comprises a first absorption layer and a second absorption layer, the first absorption layer is arranged between a liquid-permeable layer and the second absorption layer, the first absorption layer consists essentially of a carrier material coated with the thermosensitive polymer, the second absorption layer is arranged closest to a liquid-impervious layer, and the second absorption layer consists essentially of absorbent material without thermosensitive coating.

24. Absorption body according to claim 23, wherein the absorbent article is a diaper.

25. Absorption body according to claim 23, wherein the absorbent article is an incontinence protector.

26. Absorption body according to claim 23, wherein the absorbent article is a sanitary napkin.

27. Absorption material according to claim 23, wherein the cloud point is exhibited between 32° C. and 34° C.

* * * * *

UNITED STATES PATENT AND TRADEMARK OFFICE
CERTIFICATE OF CORRECTION

PATENT NO. : 6,398,769 B1
DATED : June 4, 2002
INVENTOR(S) : Maria Fernkvist et al.

It is certified that error appears in the above-identified patent and that said Letters Patent is hereby corrected as shown below:

<u>Title page,</u>
Item [22], PCT Filed: please change "Oct. 17, 1999" to -- Oct 17, 1997 --.

Signed and Sealed this

Twenty-ninth Day of October, 2002

Attest:

Attesting Officer

JAMES E. ROGAN
*Director of the United States Patent and Trademark Office*